US012680064B2

(12) United States Patent
Kim

(10) Patent No.: US 12,680,064 B2
(45) Date of Patent: Jul. 14, 2026

(54) DISPOSABLE CELL CULTURE BAG

(71) Applicant: MICRO DIGITAL CO., LTD.,
Gyeonggi-do (KR)

(72) Inventor: Kyung Nam Kim, Gyeonggi-do (KR)

(73) Assignee: MICRO DIGITAL CO., LTD.,
Gyeonggi-Do (KR)

( * ) Notice: Subject to any disclaimer, the term of this
patent is extended or adjusted under 35
U.S.C. 154(b) by 550 days.

(21) Appl. No.: 18/200,795

(22) Filed: May 23, 2023

(65) Prior Publication Data

US 2023/0313101 A1     Oct. 5, 2023

Related U.S. Application Data

(63) Continuation of application No. 16/970,973, filed as
application No. PCT/KR2019/001870 on Feb. 15,
2019, now abandoned.

(30) Foreign Application Priority Data

Feb. 19, 2018     (KR) ......................... 10-2018-0019249

(51) Int. Cl.
*C12M 1/00*        (2006.01)
*C12M 1/34*        (2006.01)
(52) U.S. Cl.
CPC ............ *C12M 23/14* (2013.01); *C12M 23/28*
(2013.01); *C12M 41/34* (2013.01)
(58) Field of Classification Search
None
See application file for complete search history.

(56) References Cited

U.S. PATENT DOCUMENTS

| | | | |
|---|---|---|---|
| 6,431,359 B1 * | 8/2002 | Hollander ............ | B65D 5/4216 |
| | | | 206/320 |
| 6,432,698 B1 | 8/2002 | Gaugler | |
| 2002/0110915 A1 | 8/2002 | Shaaltiel | |
| 2002/0131654 A1 * | 9/2002 | Smith ................ | B65D 88/1668 |
| | | | 383/96 |

(Continued)

FOREIGN PATENT DOCUMENTS

| | | |
|---|---|---|
| KR | 10-2002-0097140 A | 12/2002 |
| WO | 2012/128703 A1 | 9/2012 |
| WO | 2015/030639 A1 | 3/2015 |

OTHER PUBLICATIONS

Charter Medical product Catalog. Bio-Cube Scalable Bio Solutions
From Charter Medical (2015). See pp. 1-2.

*Primary Examiner* — Barbara J Musser
(74) *Attorney, Agent, or Firm* — Bridgeway IP Law
Group, PLLC; Sang Ho Lee; Hyun Woo Shin

(57)     ABSTRACT

Disclosed is a disposable cell culture bag capable of facili-
tating cell culture by using a flexible transparent resin film,
the disposable cell culture bag including a body having a
sealed space for accommodating a medium, and made of a
flexible transparent resin film usable for disposable prod-
ucts, and one or more tubing lines extending from an inside
to an outside of the body, wherein the body includes a
bottom-side integrated part provided by extending one or
more side surfaces from a bottom surface of the body to be
spread in a radial shape, in order to obtain continuously
smooth four edges of the bottom surface, and a top surface
fusion bonded to the side surfaces of the bottom-side inte-
grated part after the side surfaces are fusion bonded to each
other.

8 Claims, 5 Drawing Sheets

(56)  References Cited

U.S. PATENT DOCUMENTS

| 2006/0065310 A1 | 3/2006 | West |
| 2009/0035856 A1 | 2/2009 | Galliher |
| 2011/0151552 A1 | 6/2011 | Jiang |
| 2015/0299631 A1 | 10/2015 | Prabhakarpandian |
| 2016/0095279 A1 | 4/2016 | Brown |
| 2018/0010082 A1 | 1/2018 | Jaques |
| 2018/0155076 A1* | 6/2018 | Givens, Jr. ............ B32B 15/043 |
| 2019/0135483 A1* | 5/2019 | Moon ...................... B65D 5/68 |

* cited by examiner

DISPOSABLE CELL CULTURE BAG

CROSS REFERENCE TO RELATED APPLICATION

The present invention is a continuation of U.S. Ser. No. 16/970,973, filed Aug. 19, 2022 now abandoned, which is a 371 of International Application No. PCT/KR2019/001870, filed Feb. 15, 2019, which claims the benefit of KR Application No. 10-2018-0019249, filed Feb. 19, 2018, the contents of which are incorporated herein by reference.

TECHNICAL FIELD

The present invention relates to a disposable cell culture bag, and more particularly, to a disposable cell culture bag capable of facilitating cell culture by using a flexible transparent resin film.

BACKGROUND ART

In the industry for culturing animal or plant cells, a variety of devices, e.g., a cell culture device capable of culturing animal or plant cells in a medium, an isolation and purification device for isolating desired cells from the medium, a medium mixing device for mixing the medium for an appropriate culture environment, and a genetic manipulation device, may be generally used.

Due to the recent growth of the animal or plant cell culture industry, a variety of small and large culture vessels capable of safely accommodating a medium for cell culture and providing an appropriate culture environment may be applied to cell culture systems used in biological processes.

DETAILED DESCRIPTION OF THE INVENTION

Technical Problem

However, the above-described conventional culture vessels, which are generally made of a heavy and solid material, e.g., glass, metal, or plastic resin, require a high production cost for materials and processes, e.g., molding, assembling, and welding, and need to be cleaned for reuse, thereby causing a large number of problems.

In addition, the conventional culture vessels generally have a cube or cuboid shape and, particularly, four edges are sharply bent at a right angle from a rectangular bottom surface of the culture vessel for accommodating a medium. The medium may be unavoidably stagnated at the four edges of the bottom surface and thus cells may be abnormally cultured due to the stagnation. For example, cells not supplied with sufficient nutrients or oxygen may die, degenerate, or exhibit a different result due to a changed growing condition.

The present invention provides a disposable cell culture bag capable of providing a space for accommodating a medium, by fusion bonding a flexible transparent resin film, of reducing a material cost, a production cost, and a cleaning cost of products and lowering a unit cost of the products by smoothly bending edges of a bottom surface by using the flexibility, of normally culturing cells by preventing stagnation of the medium, of facilitating usage and handling by reducing weights of the products, and of allowing an air-filled and sealed state and a sterilized state of the products to be easily checked because the products are providable after being tightly filled with air and then sealed. However, the scope of the present invention is not limited thereto.

Technical Solution

According to an aspect of the present invention, there is provided a disposable cell culture bag including a body having a sealed space for accommodating a medium, and made of a flexible transparent resin film usable for disposable products, and one or more tubing lines extending from an inside to an outside of the body, wherein the body includes a bottom-side integrated part provided by extending one or more side surfaces from a bottom surface of the body to be spread in a radial shape, in order to obtain continuously smooth four edges of the bottom surface, and a top surface fusion bonded to the side surfaces of the bottom-side integrated part after the side surfaces are fusion bonded to each other.

The bottom-side integrated part may include first fusion bonding lines at boundaries and be provided in a cross shape by extending four side surfaces from the bottom surface.

The top surface may have a rectangular shape corresponding to the side surfaces of the bottom-side integrated part, and include second fusion bonding lines at boundaries.

Each of the tubing lines may include a tube penetrating through the body, and a flange protruding in an outer circumferential direction of the tube to fix the tube to the body, and fusion bonded to an internal surface of the body.

The tubing lines may include one or more of a temperature sensor line, a sampling line, a feeding line, a gas-in line, a gas-out line, an air line, a base line, and a combination thereof.

Ends of the tubing lines may be sealed with fasteners to prevent external air from entering while air is tightly filled in the body.

The tubing lines may extend along the side surfaces of the body to the bottom surface to minimize bubbles formed when a gas or a liquid is supplied from outside to the medium.

A patch for measuring an acid level and a patch for measuring an oxygen saturation level may be provided in the body.

Fusion bonded wings may be provided outside the body.

Advantageous Effects

As described above, according to some embodiments of the present invention, a space for accommodating a medium may be provided by fusion bonding a flexible transparent resin film usable for disposable products, a material cost, a production cost, and a cleaning cost of products may be reduced and a unit cost of the products may be lowered by smoothly bending edges of a bottom surface by using the flexibility, cells may be normally cultured by preventing stagnation of the medium, usage and handling may be facilitated by reducing weights of the products, and an air-filled and sealed state and a sterilized state of the products may be easily checked because the products are providable after being tightly filled with air and then sealed. However, the scope of the present invention is not limited to the above-described effects.

BEST MODE

Figure 1:
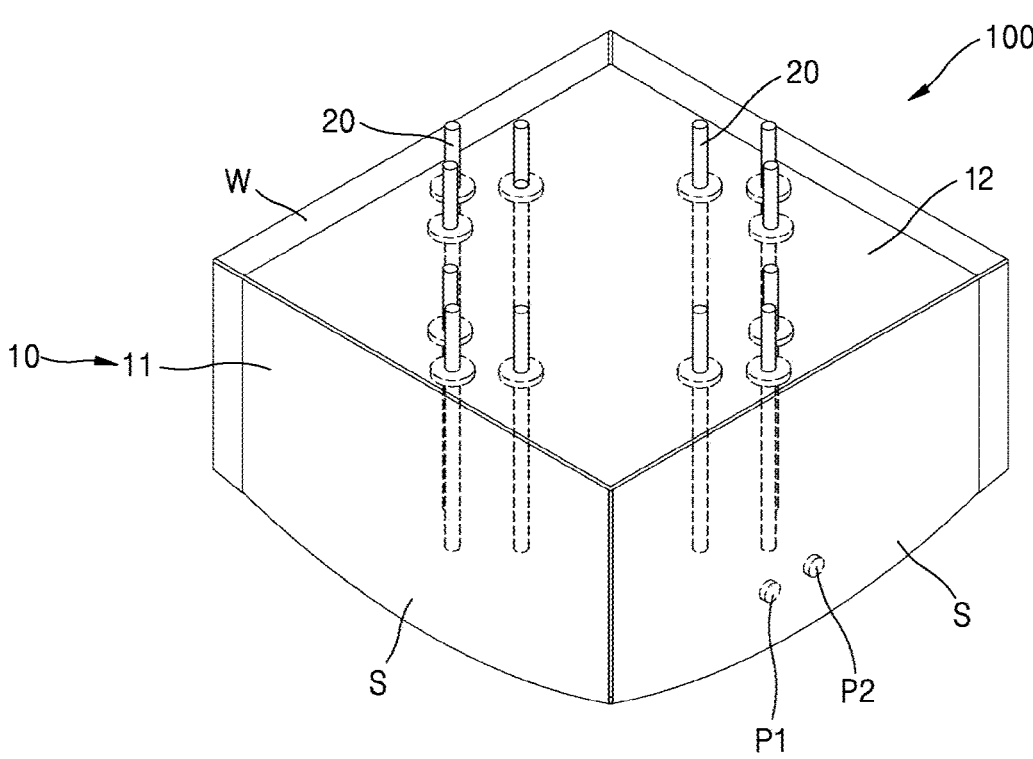
FIG. 1 is a perspective view of a disposable cell culture bag according to some embodiments of the present invention.

Hereinafter, the present invention will be described in detail by explaining embodiments of the invention with reference to the attached drawings.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the thicknesses or sizes of layers are exaggerated for clarity and convenience of explanation.

The terminology used herein is for the purpose of describing particular embodiments and is not intended to limit the invention. As used herein, the singular forms "a", "an", and "the" are intended to include the plural forms as well, unless the context clearly indicates otherwise. It will be understood that the terms "comprises" and/or "comprising", when used in this specification, specify the presence of stated features, integers, steps, operations, elements, components, and/or groups thereof, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, the embodiments of the invention should not be construed as limited to the particular shapes of regions illustrated herein, but are to include deviations in shapes that result, for example, from manufacturing.

Reference will now be made in detail to embodiments of the present invention, examples of which are illustrated in the accompanying drawings.

Figure 2:
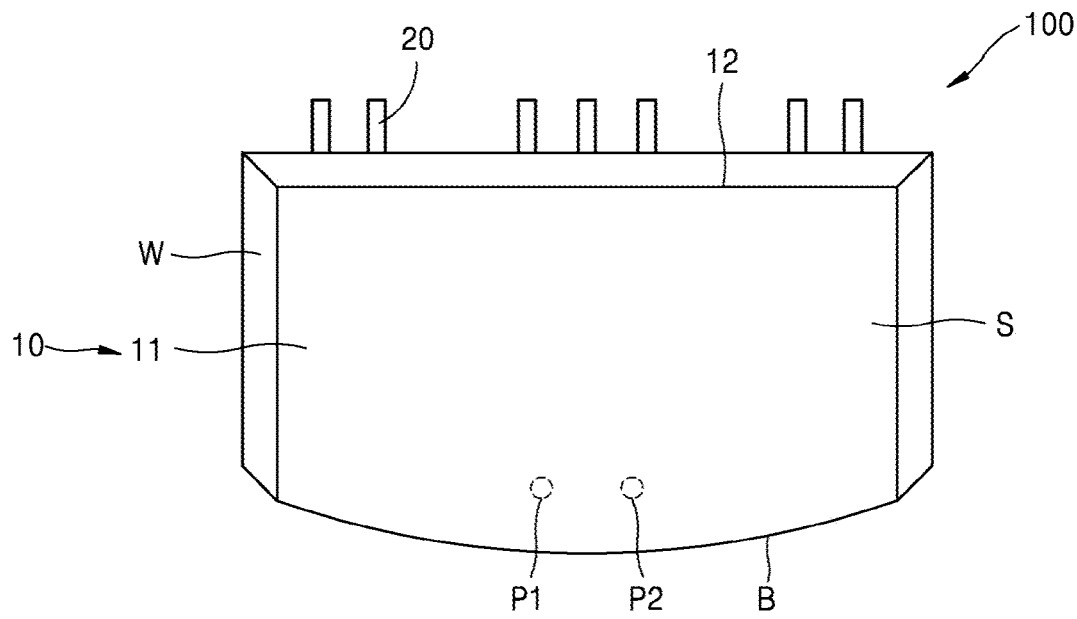
FIG. 2 is a side view of the disposable cell culture bag of FIG. 1.
Figure 3:
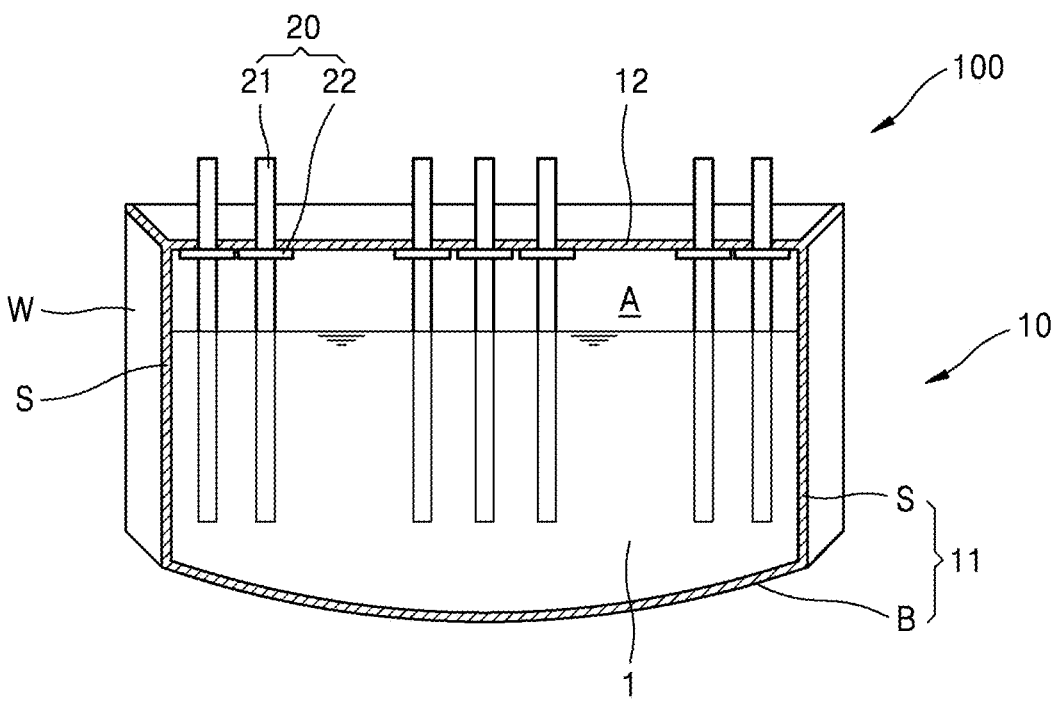
FIG. 3 is a cross-sectional view of the disposable cell culture bag of FIG. 1.
Figure 4:
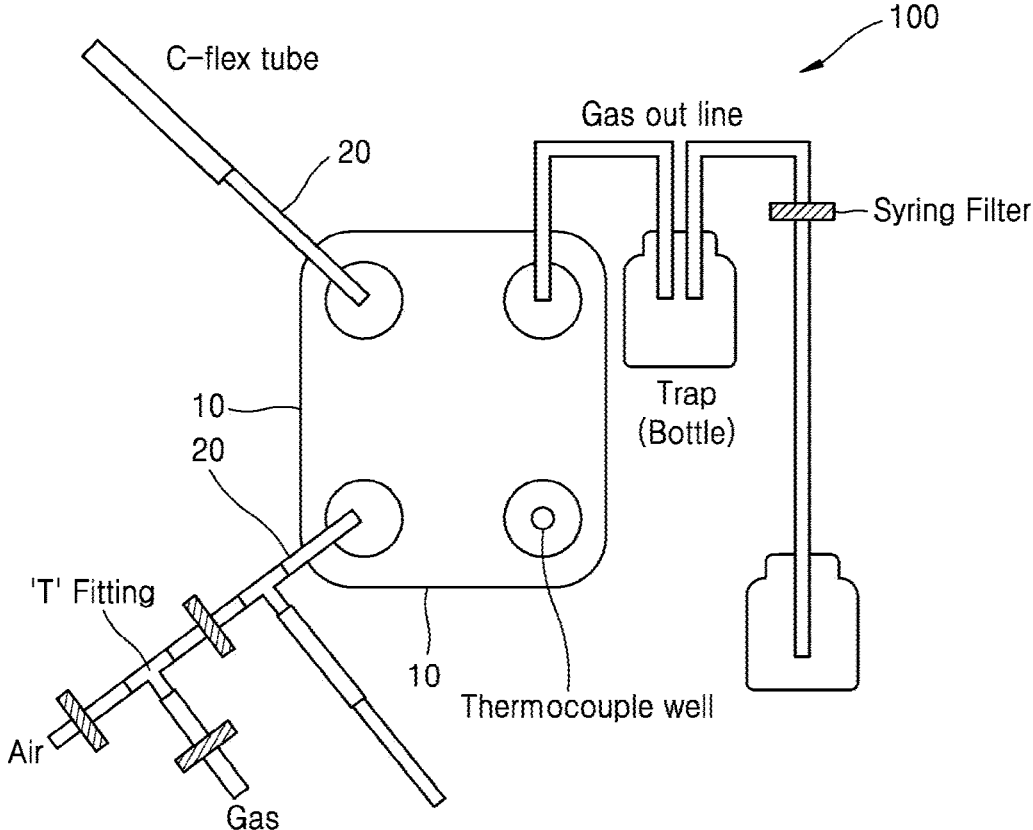
FIG. 4 is a conceptual view showing usage of the disposable cell culture bag of FIG. 1.
Figure 5:
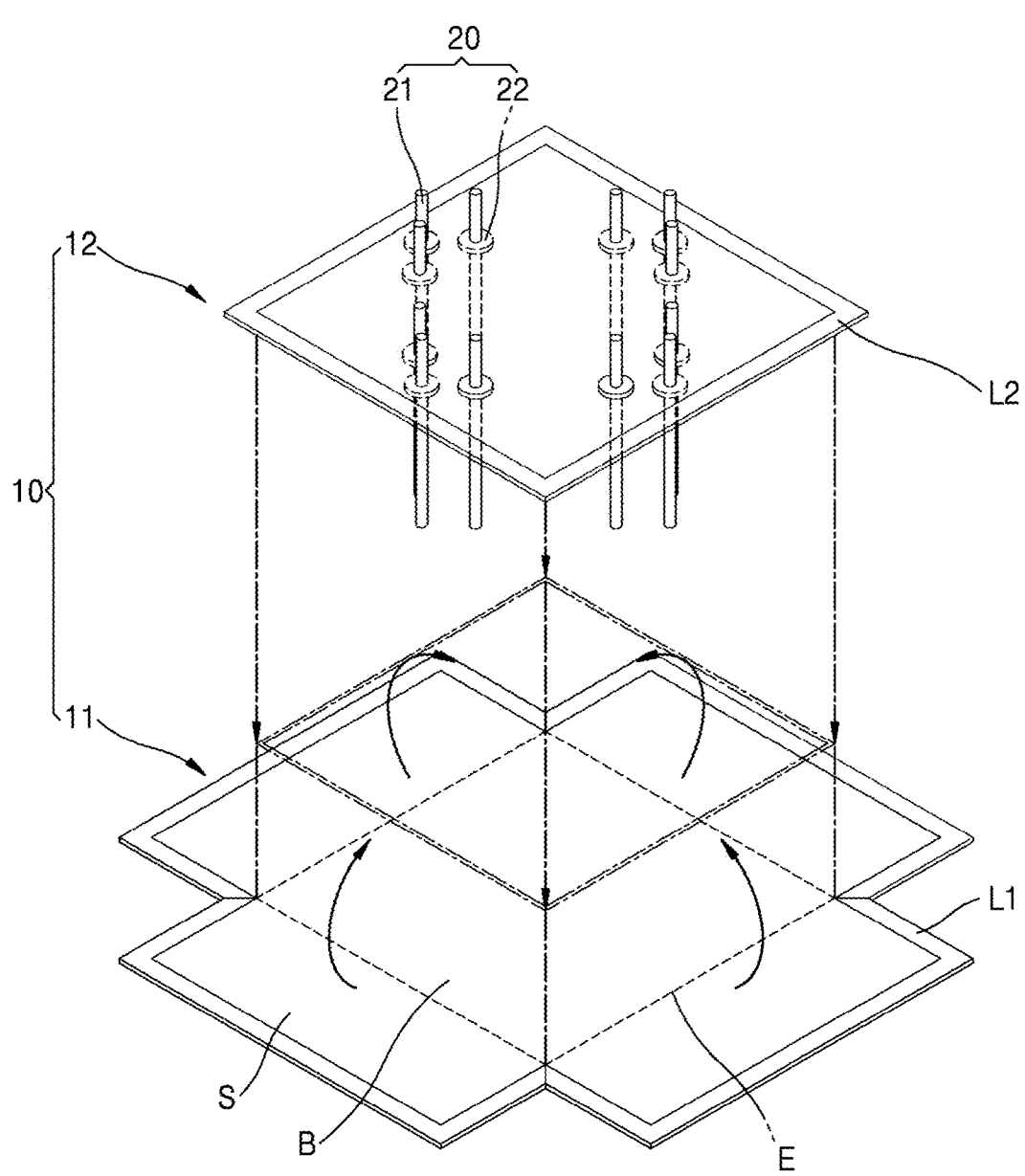
FIG. 5 is an exploded perspective view of the disposable cell culture bag of FIG. 1.

FIG. 1 is a perspective view of a disposable cell culture bag 100 according to some embodiments of the present invention. FIG. 2 is a side view of the disposable cell culture bag 100 of FIG. 1, FIG. 3 is a cross-sectional view of the disposable cell culture bag 100 of FIG. 1, FIG. 4 is a conceptual view showing usage of the disposable cell culture bag 100 of FIG. 1, and FIG. 5 is an exploded perspective view of the disposable cell culture bag 100 of FIG. 1.

Initially, as illustrated in FIGS. 1 to 5, the disposable cell culture bag 100 according to some embodiments of the present invention may mainly include a body 10 and tubing lines 20.

For example, the body 10 may have a sealed space A for accommodating a medium 1, and be made of a flexible transparent resin film usable for disposable products.

Herein, the material of the body 10 requires properties for culturing cells, e.g., gas permeability, non-toxicity, durability, and heat seal strength, and may use, for example, a wide variety of polyolefin-based, polyimide-based, polyamide-based, polypropylene-based, and polyurethane-based composites or composite materials.

Specifically, for example, as illustrated in FIGS. 1 to 5, the body 10 may include a bottom-side integrated part 11 provided by extending one or more side surfaces S from a bottom surface B of the body 10 to be spread in a radial shape, in order to obtain continuously smooth four edges E of the bottom surface B, and a top surface 12 fusion bonded to the side surfaces S of the bottom-side integrated part 11 after the side surfaces S are fusion bonded to each other.

Herein, as illustrated in FIG. 5, the bottom-side integrated part 11 includes first fusion bonding lines L1 at boundaries and is provided in a cross shape by extending four side surfaces S from the bottom surface B. However, the bottom surface B is not limited to a rectangular shape and may have a wide variety of polygonal shapes, e.g., triangular, pentagonal, and hexagonal shapes. The side surfaces S may extend from the bottom surface B in a wide variety of radial shapes. For example, three side surfaces S may be provided when the bottom surface B has a triangular shape, five side surfaces S may be provided when the bottom surface B has a pentagonal shape, and six side surfaces S may be provided when the bottom surface B has a hexagonal shape.

As illustrated in FIG. 5, the top surface 12 may have a rectangular shape corresponding to the side surfaces S of the bottom-side integrated part 11, and include second fusion bonding lines L2 at boundaries. The top surface 12 may also have a wide variety of shapes, e.g., rectangular, triangular, pentagonal, hexagonal, and polygonal shapes.

Therefore, as illustrated in FIG. 5, to form the body 10, initially, the side surfaces S of the bottom-side integrated part 11 may be folded up from the bottom surface B of the bottom-side integrated part 11 and the first fusion bonding lines L1 may be fusion bonded to each other by using heat fusion bonding, ultrasonic fusion bonding, or the like, thereby obtaining a box shape having an opening at the top.

In this case, the first fusion bonding lines L1 may be fusion bonded to each other and thus fusion bonded wings W may be provided outside the body 10 as illustrated in FIGS. 1 to 3.

Then, as illustrated in FIG. 5, the second fusion bonding lines L2 of the top surface 12 may be fusion bonded to the opening of the box shape by using heat fusion bonding, ultrasonic fusion bonding, or the like, thereby obtaining a box shape sealed in all directions.

In this case, the tubing lines 20 may be previously provided in the top surface 12.

Herein, one or more tubing lines 20 may extend from the inside to the outside of the body 10 and, as illustrated in FIGS. 1 to 5, each tubing line 20 may include a tube 21 penetrating through the body 10, and a flange 22 protruding in an outer circumferential direction of the tube 21 to fix the tube 21 to the body 10, and fusion bonded to the internal surface of the body 10.

For example, the tube 21 may be made of an elastic silicon material so as to be easily connected to other lines, and use a flexible material to be easily sealed and open.

The tubing lines 20 may include one or more of a temperature sensor line, a sampling line, a feeding line, a gas-in line, a gas-out line, an air line, a base line, and a combination thereof. However, the tubing lines 20 are not limited thereto and may include a wide variety of lines.

FIG. 4 is a conceptual view showing usage of the disposable cell culture bag 100 of FIG. 1.

As illustrated in FIG. 4, the tubing lines 20 may use various silicon tubes, C-flex tubes, or the like, and 'T' fittings, syringe filters, or trap bottles may be provided between the tubes.

Therefore, as illustrated in FIG. 4, a variety of airs, gases, base media, and discharge gases for pressure maintenance may enter or exit the body 10 by using the tubing lines 20, and a variety of sensors, e.g., a thermocouple well, may be connected to the tubing lines 20 to check an internal status.

Subsequently, after cells are cultured, the medium 1 may be taken out and then the body 10 and the tubing lines 20 may be discarded without being reused, thereby reducing a cleaning cost.

Accordingly, the space A for accommodating the medium 1 may be provided by fusion bonding the body 10 made of a flexible transparent resin film usable for disposable products, and a material cost, a production cost, and a cleaning cost of products may be reduced and a unit cost of the products may be lowered by smoothly bending the edges E of the bottom surface B by using the flexibility.

That is, as illustrated in FIG. 3, the bottom surface B provided in a round shape may prevent stagnation of the medium 1 to normally culture cells, and reduce weights of products to facilitate usage and handling.

In addition, as illustrated in FIGS. 1 and 2, a patch P1 for measuring an acid level and a patch P2 for measuring an oxygen saturation level may be provided in the body 10. However, the present invention is not limited thereto and a wide variety of patches, sensors, or pads may be provided.

Therefore, because the body 10 is made of a transparent material, a current acid level or oxygen saturation level may be easily checked with the naked eyes.

Meanwhile, as illustrated in FIG. 3, one or more of the tubing lines 20 may extend along the side surfaces S of the body 10 to the bottom surface B to minimize bubbles formed when a gas or a liquid is supplied from outside to the medium 1.

Therefore, by minimizing bubbles formed in the medium 1, cell culture efficiency may be improved and bad influence caused when a liquid or a gas enters or exits may be minimized.

Figure 6:
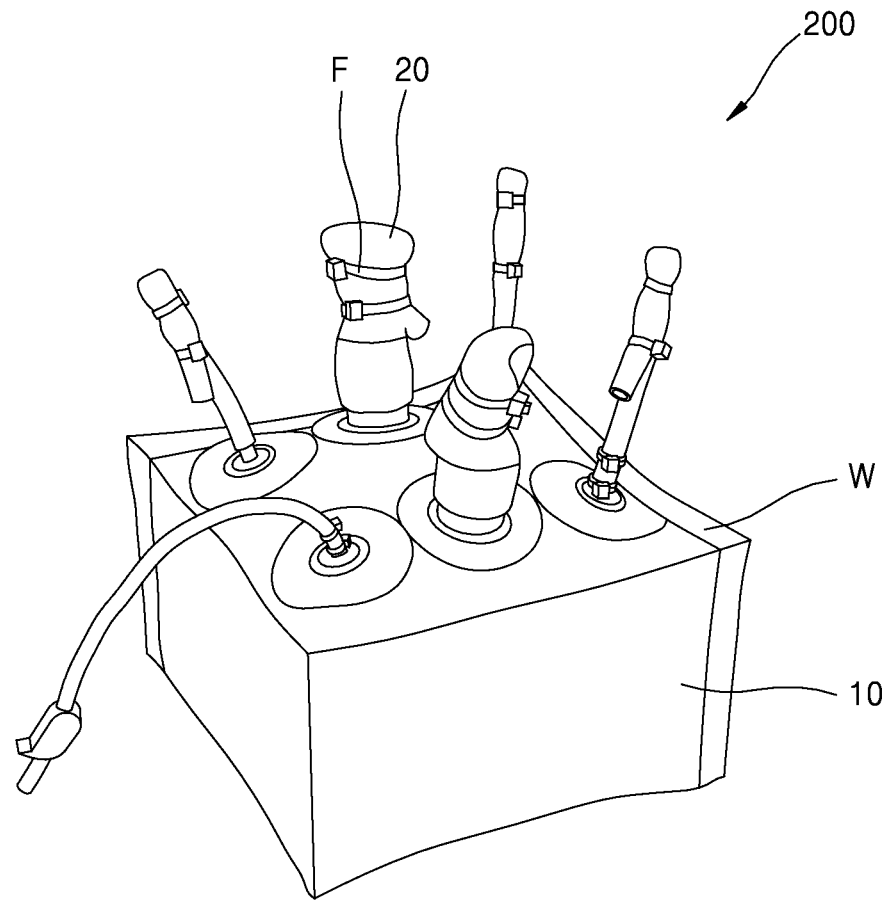
FIG. 6 is a perspective image of a disposable cell culture bag according to other embodiments of the present invention.
Figure 7:
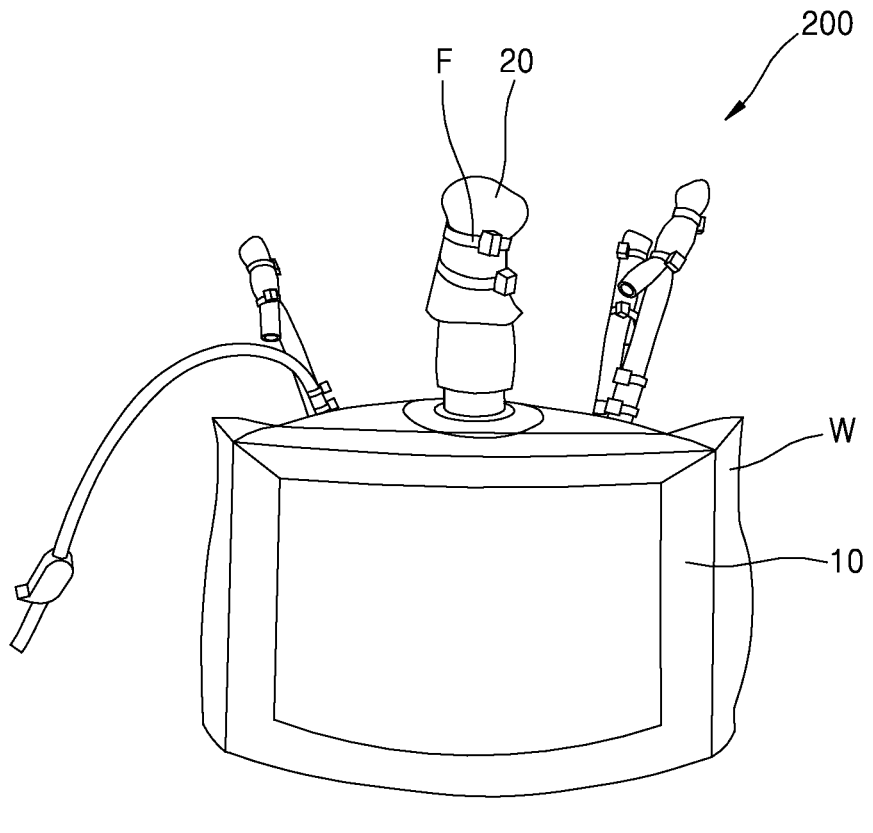
FIG. 7 is a front image of the disposable cell culture bag of FIG. 6.

FIG. 6 is a perspective image of a disposable cell culture bag 200 according to other embodiments of the present invention, and FIG. 7 is a front image of the disposable cell culture bag 200 of FIG. 6.

As illustrated in FIGS. 6 and 7, ends of the tubing lines 20 of the disposable cell culture bag 200 according to other embodiments of the present invention may be sealed with fasteners F to prevent external air from entering while air is tightly filled in the body 10.

Herein, the fasteners F may use a wide variety of fasteners, e.g., clips, strings, strips, tie bars, and fastening devices.

Accordingly, an air-filled and sealed state and a sterilized state of products may be easily checked because the products are providable after being tightly filled with air and then sealed and after being sterilized with, for example, ultraviolet (UV) light, X-rays, infrared light, or heat.

While the present invention has been particularly shown and described with reference to embodiments thereof, it will be understood by one of ordinary skill in the art that various changes in form and details may be made therein without departing from the scope of the present invention as defined by the following claims.

6

INDUSTRIAL APPLICABILITY

As described above, according to some embodiments of the present invention, a space for accommodating a medium may be provided by fusion bonding a flexible transparent resin film usable for disposable products, and a material cost, a production cost, and a cleaning cost of products may be reduced and a unit cost of the products may be lowered by smoothly bending edges of a bottom surface by using the flexibility.

The invention claimed is:

1. A method of fabricating a disposable cell culture bag, comprising:

folding up side surfaces of a bottom-side integrated part having a one-piece bottom surface and four rectangular side surfaces extending from the bottom surface, the bottom surface having a round shape and a unitary construction and being integrally formed with the one four rectangular side surfaces prior to bonding first bonding lines to one another, the first bonding lines being located at boundaries of the bottom-side integrated part, wherein the bottom-side integrated part is provided in a cross shape formed by the four rectangular side surfaces extending from the bottom surface without touching each other in combination with the bottom surface having the round shape;

fusion bonding the first bonding lines to one another;

fusion bonding a top surface to the four rectangular side surfaces of the bottom-side integrated part to thereby define a body having a sealed space for accommodating a medium and being made of a flexible transparent resin film used for disposable products; and arranging one or more tubing lines so that the tubing lines extend from outside of the body, through the top surface to an inside of the body.

2. The method of claim 1, wherein the top surface has a rectangular shape corresponding to the side surfaces of the bottom-side integrated part, and comprises second fusion bonding lines at boundaries.

3. The method of claim 1, wherein each of the one or more tubing lines comprises a tube and flange, and further comprising:

fusion bonding the flange to an internal surface of the body; and penetrating the tube through the body and fixing the tube to the body by arranging the tube in the flange so that the flange protrudes in an outer circumferential direction from the tube.

4. The method of claim 1, wherein the tubing lines comprise one or more of a temperature sensor line, a sampling line, a feeding line, a gas-in line, a gas-out line, an air line, a base line, or a combination thereof.

5. The method of claim 4, further comprising sealing the one or more tubing lines with fasteners to prevent external air from entering while air is filled in the body.

6. The method of claim 1, wherein the one or more tubing lines extend along the four rectangular side surfaces of the body to the bottom surface to minimize bubbles formed when a gas or a liquid is supplied from outside to the medium.

7. The method of claim 1, further comprising providing in the body a patch for measuring an acid level and a patch for measuring an oxygen saturation level.

8. The method of claim 1, wherein fusion bonding the first bonding lines comprises providing fusion bonded wings on an outside of the body.

* * * * *